(12) United States Patent
Lister (10) Patent No.: US 10,470,657 B1
(45) Date of Patent: Nov. 12, 2019

(54) SYSTEMS AND METHODS FOR ADMINISTERING A GAZE NYSTAGMUS TEST

(71) Applicant: Thomas E. Lister, Middleton, WI (US)

(72) Inventor: Thomas E. Lister, Middleton, WI (US)

( * ) Notice: Subject to any disclaimer, the term of this patent is extended or adjusted under 35 U.S.C. 154(b) by 0 days.

(21) Appl. No.: 16/288,235

(22) Filed: Feb. 28, 2019

(51) Int. Cl.
| | |
|---|---|
| A61B 3/00 | (2006.01) |
| A61B 3/113 | (2006.01) |
| A61B 5/0496 | (2006.01) |
| A61B 5/00 | (2006.01) |

(52) U.S. Cl.
CPC ............ *A61B 3/113* (2013.01); *A61B 5/0496* (2013.01); *A61B 5/4863* (2013.01); *A61B 3/005* (2013.01); *A61B 5/4845* (2013.01)

(58) Field of Classification Search
CPC ..... A61B 3/113; A61B 5/4863; A61B 5/0496; A61B 3/005; A61B 5/4845; A61F 2009/00846
USPC ........................................................ 351/209
See application file for complete search history.

(56) References Cited

U.S. PATENT DOCUMENTS

| | | | |
|---|---|---|---|
| 5,784,145 A | 7/1998 | Ghodse et al. |
| 7,357,507 B2 | 4/2008 | Waldorf et al. |
| 7,448,753 B1 | 11/2008 | Chinnock |
| 7,614,745 B2 | 11/2009 | Waldorf et al. |
| 7,798,643 B2 | 9/2010 | Waldorf et al. |
| 8,585,609 B2 | 11/2013 | Kiderman et al. |
| 8,899,748 B1 | 12/2014 | Migdal |
| 9,039,631 B2 | 5/2015 | Kiderman et al. |
| 9,039,632 B2 | 5/2015 | Kiderman et al. |
| 9,198,571 B2 | 12/2015 | Kiderman et al. |
| 9,247,870 B2 | 2/2016 | Kiderman et al. |
| 9,301,675 B2 | 4/2016 | Kiderman et al. |
| 9,357,918 B1 | 6/2016 | Cohen |
| 9,357,966 B1 | 6/2016 | Cohen |
| 9,596,986 B2 | 3/2017 | Kiderman et al. |
| 9,700,203 B1 | 7/2017 | Harris |
| 9,723,981 B2 | 8/2017 | Kiderman et al. |
| 2007/0236663 A1 | 10/2007 | Waldorf et al. |
| 2009/0132275 A1 | 5/2009 | Jung et al. |

(Continued)

FOREIGN PATENT DOCUMENTS

| | | |
|---|---|---|
| CN | 104814717 B | 9/2016 |
| WO | WO2015120438 A1 | 8/2015 |

(Continued)

OTHER PUBLICATIONS

DWI Detection and Standardized Field Sobriety Testing (SFST) Refresher Manual, National Highway Traffic Safety Administration (NHTSA), Oct. 2015, 98 Pages.

*Primary Examiner* — William R Alexander
*Assistant Examiner* — Henry A Duong
(74) *Attorney, Agent, or Firm* — Smith Keane LLP (57) ABSTRACT

Systems and methods for performing a Horizontal Gaze Nystagmus (HGN) test. An HGN test device having a harness configured to be worn by a subject, a moveable stimulus controlled by a computing device, and a recording device for recording the eyes of the subject during the administration of the HGN test. More specifically, the HGN device has a movable armature or an arm with a stimulus there attached which follows a track. The recording may be stored in the computing device or transmitted to a remote system for storage.

13 Claims, 6 Drawing Sheets

(56) References Cited

U.S. PATENT DOCUMENTS

| | | | |
|---|---|---|---|
| 2009/0216092 A1* | 8/2009 | Waldorf | A61B 3/005 600/301 |
| 2010/0016754 A1 | 1/2010 | Whitlock et al. | |
| 2010/0280372 A1 | 11/2010 | Poolman et al. | |
| 2011/0085135 A1 | 4/2011 | Bertolli | |
| 2011/0176106 A1 | 7/2011 | Lewkowski | |
| 2013/0057829 A1 | 3/2013 | Harris et al. | |
| 2014/0141456 A1* | 5/2014 | Kumar | G01N 33/689 435/7.92 |
| 2014/0171756 A1* | 6/2014 | Waldorf | A61B 3/032 600/301 |
| 2014/0294245 A1 | 10/2014 | Siilats | |
| 2014/0313488 A1 | 10/2014 | Kiderman et al. | |
| 2015/0085252 A1 | 3/2015 | Fujimura et al. | |
| 2015/0245766 A1 | 9/2015 | Rennaker et al. | |
| 2015/0335278 A1 | 11/2015 | Ashmore et al. | |
| 2016/0007921 A1 | 1/2016 | Galea et al. | |
| 2016/0081546 A1 | 3/2016 | MacDougall | |
| 2016/0166193 A1 | 6/2016 | Lin et al. | |
| 2016/0270711 A1 | 9/2016 | Ashmore et al. | |
| 2016/0339922 A1 | 11/2016 | Schmidt | |
| 2017/0007119 A1 | 1/2017 | Cornsweet et al. | |
| 2017/0105669 A1 | 4/2017 | Valenti | |
| 2019/0254754 A1* | 8/2019 | Johnson | A61B 34/20 |

FOREIGN PATENT DOCUMENTS

| | | | |
|---|---|---|---|
| WO | WO2016092563 A2 | 6/2016 | |
| WO | WO2017091909 A1 | 6/2017 | |
| WO | WO2017119659 A1 | 7/2017 | |

* cited by examiner

SYSTEMS AND METHODS FOR ADMINISTERING A GAZE NYSTAGMUS TEST

BACKGROUND OF THE INVENTION

Nystagmus is an involuntary jerking or bouncing of the eyeball that occurs when there is a disturbance of the vestibular (inner ear) system or the oculo-motor control of the eye. Horizontal gaze nystagmus (HGN) refers to a lateral or horizontal jerking when the eye gazes to the side. In the impaired driving context, alcohol consumption or consumption of certain other central nervous system depressants, inhalants or phencyclidine, hinders the ability of the brain to correctly control eye muscles causing the jerk or bounce associated with HGN. As the degree of impairment becomes greater, the jerking or bouncing of the nystagmus becomes more pronounced. This is assessed in the horizontal gaze nystagmus test.

The horizontal gaze nystagmus test is one of three field sobriety tests that comprise the standardized field sobriety test (SFST) battery (the other two tests are the walk-and-turn test and the one-leg-stand test) of the National Highway Traffic Safety Administration (NHTSA). Scientific evidence has shown the horizontal gaze nystagmus test as a reliable roadside measure of a person's impairment due to alcohol or certain other drugs.

Nystagmus describes the "bouncing" eye motion displayed in two ways: (1) pendular nystagmus, where the eye oscillates equally in two directions, and (2) jerk nystagmus, where the eye moves slowly away from a fixation point and then is rapidly corrected through a saccadic (fast) movement. HGN is a type of jerk nystagmus with the saccadic movement toward the direction of the gaze.

An eye normally moves smoothly, whereas an eye with jerk nystagmus moves like a marble rolling across sandpaper. Most types of nystagmus, including HGN, are involuntary motions, meaning the person exhibits the nystagmus without control. The subject exhibiting nystagmus is unaware that it is happening because the bouncing of the eye does not affect the subject's vision.

Law enforcement officers have used field sobriety tests (FST) to detect impairment and to develop probable cause to arrest. Most FSTs test coordination, Balance, and dexterity. The HGN test tracks the movement or coordination and balance of the eye.

The HGN test requires an object for a subject to follow with their eye, such as a pen or the tip of a penlight. The officer places the object approximately twelve to fifteen inches from the subject's face and slightly higher than eye level and instructs the subject to follow the object with the eyes only with the head held still.

The officer checks for the lack of smooth pursuit by eye by moving the object slowly from the center of the subject's face towards the left ear. The left eye should smoothly follow the object, but if the eye exhibits nystagmus, the officer notes the clue. The officer then checks the right eye for the same.

Starting again from the center of the suspect's face, the officer moves the object toward the left ear, bringing the eye as far over as possible and holds the object there for four seconds. The officer notes if there is a distinct and sustained nystagmus at this point. The officer holds the object at maximum deviation for at least four seconds to ensure that quick movement of the object did not cause the nystagmus. The right eye is then checked using the same procedure. The procedure is commonly referred to as "end-point" nystagmus.

The test further requires the officer to move the object at a speed that would take about four seconds for the object to reach the edge of the suspect's left shoulder. The officer notes if the point or angle at which the eye begins to display nystagmus is before the object reaches forty-five degrees from the center of the suspect's face. The officer then moves the object towards the suspect's right shoulder.

Despite the strong correlation between alcohol consumption and HGN, some trial courts still do not admit the results of the HGN test into evidence. Additionally, even if admitted, the officer's administration of the test is often challenged. Therefore, there is a need for an HGN testing device capable of administering and recording the results of an HGN test more consistently and effectively.

SUMMARY OF THE INVENTION

The present invention relates to an HGN testing device capable of administering and recording the results of an HGN test more consistently and effectively.

The apparatus administers the test without human error following a set of accepted protocols for the administration of the test. The apparatus directs various points of light simulating the object an officer would use in directing the test subject to follow with their eyes. The apparatus tests both eyes for the exhibition of nystagmus indicating the subject may be intoxicated.

The apparatus can test and record the eye movement of a test subject for the lack of smooth eye movement in the pursuit of an object. The apparatus further tests for distinct nystagmus at a maximum deviation. Additionally, the apparatus looks at the angle of onset of nystagmus prior to forty-five degrees or when the eye begins to display nystagmus before the object reaches forty-five degrees from the center of the suspect's face.

In great detail, the apparatus for administering a horizontal gaze nystagmus test includes a harness configured to fit a human head such that the apparatus can engage the eyes of the test subject. The harness is typically adjustable and can be configured as either a cap or simply with straps.

In one embodiment, the apparatus uses a jointed armature assembly connected to the harness having a first and second end, wherein the second end includes a distinct terminus. The distinct terminus is the point to which the subject's eyes must follow. In an embodiment the terminus is a small light emitting diode (LED). The apparatus further includes a motor operatively connected and driving the second end of the jointed armature assembly. The device also includes a computing device operatively connected to the motor whereby the movements of the armature assembly can be directed. The computing device may be program logic controller (PLC) capable of directing the armature about a preprogramed path. A power supply is included which is operatively connected to the motor, computing device and light source. The power supply can include a battery.

The apparatus also includes a recording device affixed to the harness whereby the movement of the eyes can be recorded in response to the movement of the distinct terminus end of the armature. The recording device can be selectively detachable to the harness wherein an attachment device is operatively configured to receive and power such a device on the harness. The recording device can capture either visual images, audio signals or both.

A further embodiment includes both a harness and a visor attached to the harness. The visor is operatively aligned in front of the subject's eyes whereby the visor screens the subject's eyes. A projector is included and attached to the harness for displaying a distinct light source onto the visor. The projector can move the light source about an eye facing surface of the visor for the subject's eye to follow. A computing device is operatively connected to the projector whereby the movements of the light source can be directed and a power supply operatively connected to the projector and computing device.

Additionally included in a further embodiment is a display screen attached to the harness and operatively aligned in front of the subject's eyes wherein a distinct point of light is displayed on the screen and visible to the subject's eyes. The apparatus also includes a computing device operatively connected to the screen whereby the movement of the distinct point of light can be directed about the screen and a power supply operatively connected to the screen and computing device. The apparatus can also include a recording device affixed to the harness whereby the movement of the eyes can be recorded in response to the movement of the light sources.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
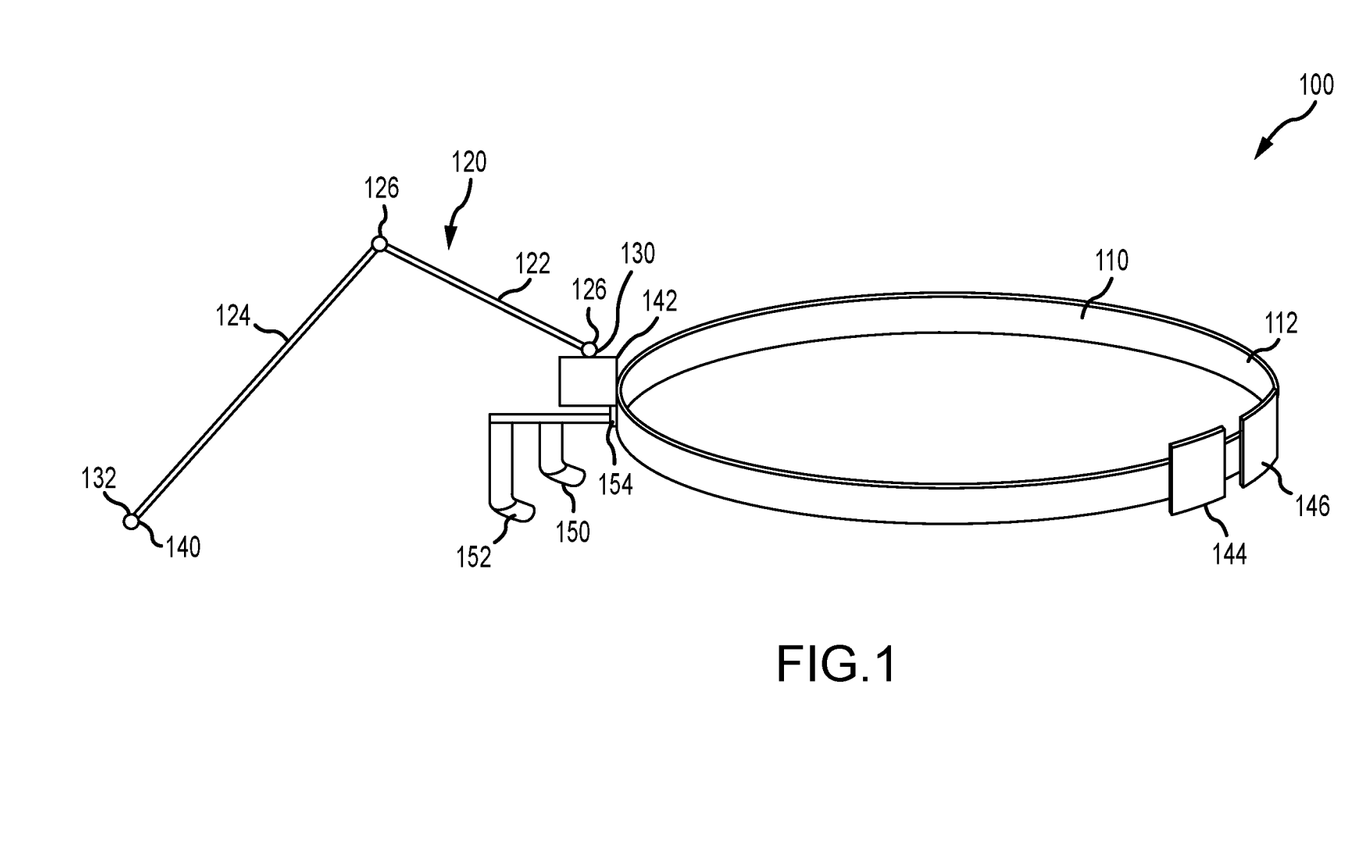
FIG. 1 is a perspective view of a first embodiment of a horizontal gaze nystagmus (HGN) test device according to the present invention.

FIG. 1 shows a first exemplary embodiment 100 of the Horizontal Gaze Nystagmus (HGN) test device according to the present invention. The HGN test device 100 preferably has a harness 110, an armature assembly 120 driven by a motor 142, a recording device 152 (e.g., an image sensor or video camera), a computing device 144, a light 150, and a power supply 146.

Figure 3A:
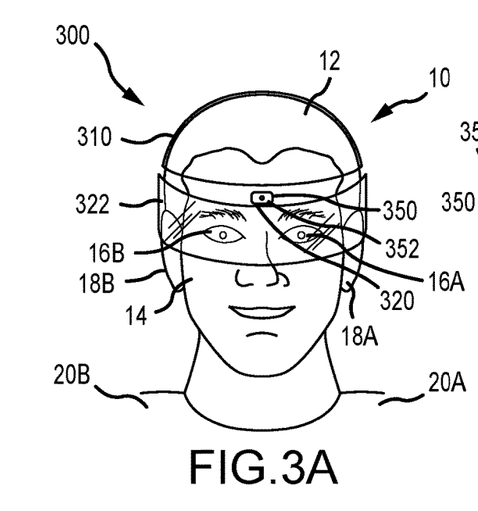
FIG. 3A is a front elevation view of a third embodiment of an HGN test device according to the present invention.

The harness 110 is preferably configured to be worn about the head 12 of a test subject 10 (see FIG. 3A). The harness 110 may be adjustable. For example, the harness may have adjustable straps (see FIG. 3) or an elastic band 112 as shown.

The armature assembly 120 preferably includes a plurality of articulated arms (here shown as a first armature member 122 and a second armature member 124) having one or more joints 126 and extending between a first end 130 and a second end 132. A visual stimulus 140 is preferably positioned on the second end 132 and the first end 130 is preferably operatively connected to the motor 142.

The stimulus 140 may include any object capable of being followed by the human eye. For example, and not by limitation, the stimulus 140 may be a small pigmented ball mounted to the end of the armature and/or a light source such as a light emitting diode (LED). It is further contemplated that the stimulus 140 may have various shapes and colors, including objects which luminesce.

The motor 142 is preferably a servomotor with a rotary actuator (not shown); however, any motor capable of performing the functions as disclosed herein may be used. Additionally, or alternatively, a plurality of motors 142 may be utilized according to the present invention. A controller is preferably operatively connected to the motor 142 to control motor direction and/or speed.

The recording device 152 is preferably attached to the harness 110 and positioned to record the movement of the subject's eyes 16A,16B (see FIG. 3A) in response to the movements of the stimulus 140. The recording device 152 may be selectively detachable from the harness 110 through an attachment device 154, such as a clip and socket configuration. Of course, other known configurations for attaching the recording device 152 to the harness 110 can be used.

The recording device 152 and/or controller may be configured to store any recordings as an electronically accessible record (such as an image format (e.g., *.tif, *.jpg, *.gif, or *.png file) or encoded video format (e.g., MPEG, H.261, H.263, H.264)) within internal memory storage (not shown) in the recording device (e.g., an SD card) or memory otherwise mounted to the harness 110, and/or configured to transmit the electronically accessible record or a copy thereof to an external storage device (e.g., a nonvolatile electronic memory such as a storage medium (server) that is accessible over a network, such as the internet (not shown) via a wired connection and/or wireless transmission (e.g., BLUETOOTH® communication, IEEE 802.11 wireless communication). More preferably, simultaneously with the creation or transmission of the electronically accessible record, or preferably soon thereafter, and as a result thereof, a chain of custody record is created and associated with the electronically accessible record. The chain of custody record preferably includes information related to at least one of, but preferably all of, the following: date of creation of the electronically accessible record, time of creation of the electronically accessible record, geographic location of the creation of the electronically accessible record, a name of a human whose eyes were visually recorded in the electronically accessible record, direction and duration of movements of the stimulus during creation of the electronically accessible record, and/or a name of a human who caused the creation of the electronically accessible record.

The recording device 152, when secured to the harness 152 or otherwise positioned for use with respect to a subject's head, is configured to capture still images and/or video sequences from a focal field of about 5 to about 7 inches wide—but in any event at least as wide as a subject's bizygomatic breadth (maximum horizontal breadth between the zygomatic arches)—by about 1 to about 3 inches tall, at a distance of about 10 to about 18 inches from the stimulus 140, measured towards the first end 130 along a subject's sagittal plane when the harness is mounted thereto.

Additionally or alternatively, the recording device 152 may record audio and/or other images such as surface temperature through thermal imaging.

The light 150 (e.g., a diffused light to simply illuminate the face 14 sufficiently to enable observation and/or recording of eye movement) is preferably attached to the harness 110 and aimed at the face 14 of the subject 10 to illuminate the subject's eyes 16A,16B during the administration of the HGN test.

The computing device 144 is preferably in operative communication with the motor 142, the recording device 152, and/or the light 150. The computing device 144 is preferably configured to administer the HGN test and operate the recording device 152 and the light 150. The computing device 144 may be attached to the harness 110 as shown in FIG. 1 or it may be located remotely. The computing device 144 may be wired to the motor 142, the recording device 152, and the light 150 or it may be in wireless communication therewith (e.g., BLUETOOTH® communication, IEEE 802.11 wireless communication).

The power supply 146 is preferably attached to the harness 110 and configured to provide power to the motor 142, the recording device 152, the computing device 144 (if located on the harness 110), and the light 150.

The HGN test device 100 is preferably configured to allow administration of the HGN test pursuant to a method of following a set of protocols. The term "HGN" is used to indicate horizontal gaze nystagmus and the test protocols associated with observing HGN. If the test protocols are modified, the HGN test device 100 may be programed to include and perform such modifications within the limitations of the hardware of the HGN test device 100. It is contemplated that the computing device 144 is programmable and can be instructed to perform additional tasks as the HGN test evolves.

The device 100 may be secured at least substantially stationary to a subject's head such that the stimulus 140 is positioned about ten to about eighteen inches (more preferably about twelve to about fifteen inches) from the subject's nose, and the subject 10 is instructed to follow the stimulus 140 with their eyes 16A,16B. The HGN test device 100 is preferably configured to test both eyes 16A,16B for the exhibition of nystagmus indicating the subject may be intoxicated.

The HGN test device 100 is preferably configured to elucidate the three main clues of intoxication under the HGN test. The first is the lack of smooth pursuit of the eye as it follows the stimulus 140. During the testing of a subject's left eye 16A, the stimulus 140 moves slowly from the center of the subject's face 14 (e.g., at least approximately aligned with the sagittal plane of the subject's face) toward the left ear 18A (e.g., along a substantially transverse plane), and similarly, for testing the subject's right eye 16B, the stimulus 140 starts at the center of the subject's face 14 (e.g., at least approximately aligned with the sagittal plane of the subject's face) and moves slowly toward the right ear 18B (e.g., along a substantially transverse plane). Preferably, both the left and the right eye 16A,16B are tested during the HGN test. If the movement of either of the subject's eyes 16A,16B is not smooth in the movement direction of the stimulus 140 (i.e., pausing, jerking or bouncing) the eye 16A,16B exhibits a nystagmus and the person is likely to be intoxicated.

The second test is the discovery of a distinct nystagmus at a set maximum deviation or an end point nystagmus. In this test the subject 10 is required to follow the stimulus 140 of the HGN test device 100 as moves from the center of the subject's face 14 toward the left ear 18A and stops at a predetermined location, typically just within eyesight, and the stimulus 140 remains in this position for a set period of time, preferably about four seconds. If a distinct and sustained nystagmus is observed in the left eye 16A, the subject 10 is likely to be intoxicated. The same procedure is performed looking for nystagmus in the right eye 16B by moving the stimulus 140 from the center of the subject's face 14 toward the right ear 18B and stopping at a predetermined location, typically just within eyesight, and the stimulus 140 remains in this position for a set period of time, preferably about four seconds.

The third test includes the detection of the onset of nystagmus prior to reaching a forty-five-degree angle defined from the centerline of the subject's face 14 and rotating radially toward the subject's left or right shoulder 20A,20B. The stimulus 140 is preferably moved at a constant speed, preferably a speed that would take about four seconds for the stimulus 140 to simulate an object reaching the edge of a subject's shoulder 20A,20B. For the left eye 16A, the stimulus 140 rotates toward the left shoulder 20A and for the right eye 16B the stimulus 140 rotates toward the right shoulder 20B. Preferably, all three tests are administered to determine if nystagmus is present.

For any of the exemplary embodiments, an indicator (visual and/or audible; not shown) can indicate to the administrator whether the subject passes or fails any of the HGN tests. For example, a green light can indicate the subject 10 passed the HGN test and is not impaired and a red light can indicate that the subject 10 failed the HGN test and is likely impaired. A notification of the HGN test results can be sent to the computing device 144 and stored and/or forwarded to a remote site (not shown), for example, a police station.

Additionally, or alternatively, the HGN test device 100 may check for vertical nystagmus. Vertical nystagmus may be checked by moving the stimulus 140 several inches above a subject's eyes 16A,16B. While vertical nystagmus is not part of the typical HGN test, it is a good indicator of consumption of high doses of alcohol. The capability to perform such a test may be included in an embodiment of the HGN test device 100 and in the testing procedures administered to the subject with the HGN test device 100.

Figure 2:
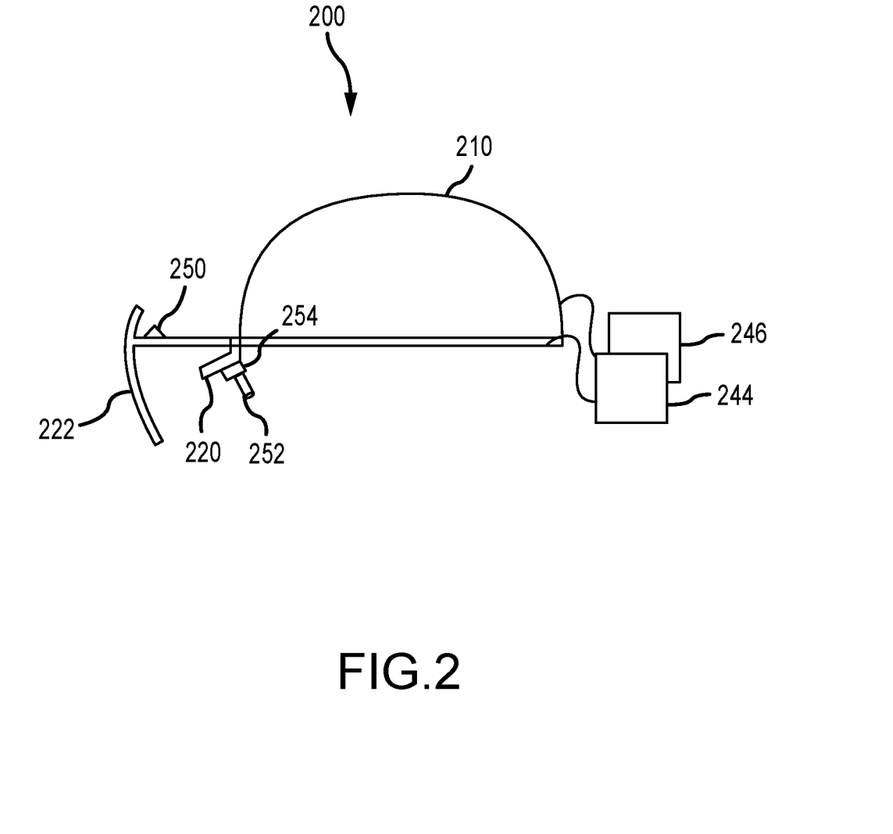
FIG. 2 is a side elevation view of a second embodiment of an HGN test device according to the present invention.

FIG. 2 shows a second embodiment 200 of the HGN test device. The HGN test device 200 has a projector 220 mounted to a harness 210 preferably configured to project a distinct point of light (not shown) onto a screen 222. The harness 210 illustrated in FIG. 2 is a cap design configured to mostly fit about the top of a subject's head 12. The screen 222 is preferably curved and positioned outward from the subject's face 14 to encompass a substantial portion of the subject's field of vision.

Similar to the first embodiment 100, the HGN test device 200 preferably has a light 250 for illuminating the subject's eyes 16A,16B, a recording device 252 such as a camera positioned to record movement of the subject's eyes 16A, 16B mounted to the harness 210 with an attachment device 254, a computing device 244, and a power supply 246.

The subject is instructed to follow the point of light (not shown) from the projector 220 with his eyes 16A,16B according to the HGN protocol described above. A computing device 244 controls the projector 220 and commands the projector 220 to project the point of light onto the screen 222 and move the light about the screen 222. Preferably, the screen 222 is transparent from a HGN test administrator's perspective so that the eyes 16A,16B of the subject 10 may be observed. The elements common to those in the first embodiment 100 may be attached and configured in the same way as applied to second embodiment 200.

Figure 3B:
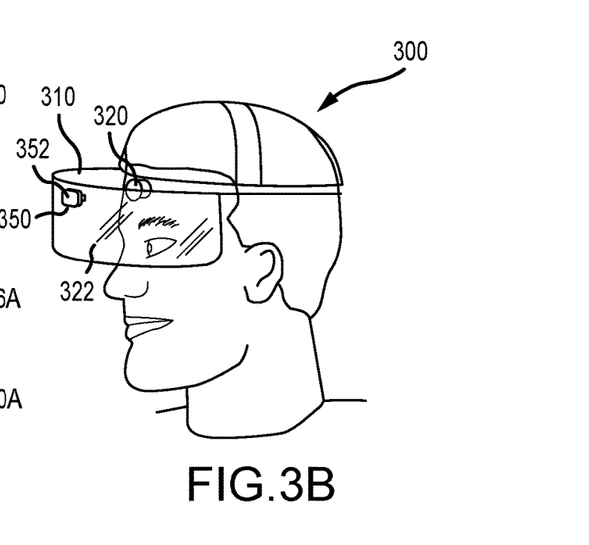
FIG. 3B is side elevation view of the HGN test device shown in FIG. 3A.
Figure 3C:
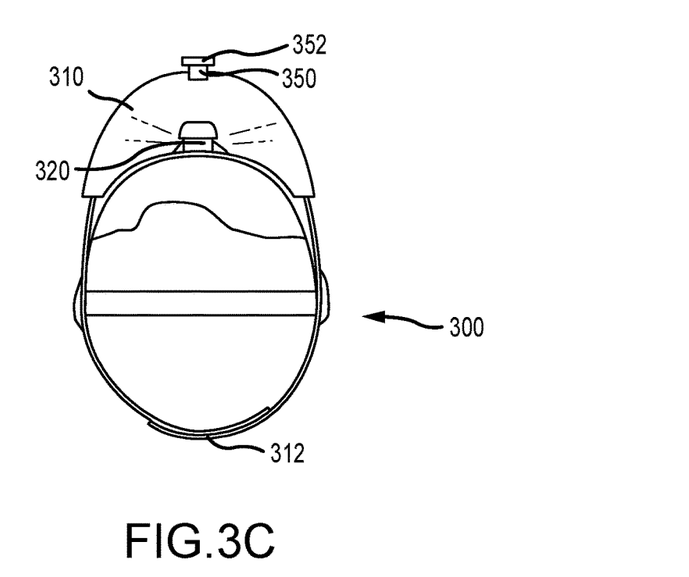
FIG. 3C is a top plan view of the HGN test device shown in FIG. 3A.

FIG. 3 depicts a third embodiment 300 of an HGN test device according to the present invention similar to that of the second embodiment HGN test device 200 shown in FIG. 2. The HGN test device 300 has a projector 320 mounted to a harness 310 preferably configured to project a distinct point of light (not shown) onto a screen 322. The harness 310 illustrated in FIG. 3 wraps around a subject's head 12 and has adjustable straps 312 configured to be adjustable to provide a secure fit.

The screen 322 is preferably curved and positioned outward from the subject's face 14 to encompass a substantial portion of the subject's field of vision. The HGN test device 300 preferably has a light 350 for illuminating the subject's eyes 16A,16B and a recording device 352 such as a camera positioned to record movement of the subject's eyes 16A, 16B and is mounted to the screen 322.

Figure 4A:
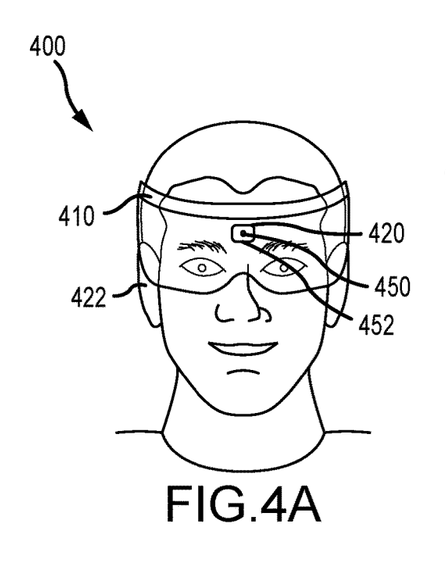
FIG. 4A is a front elevation view of a fourth embodiment of an HGN test device according to the present invention.
Figure 4B:
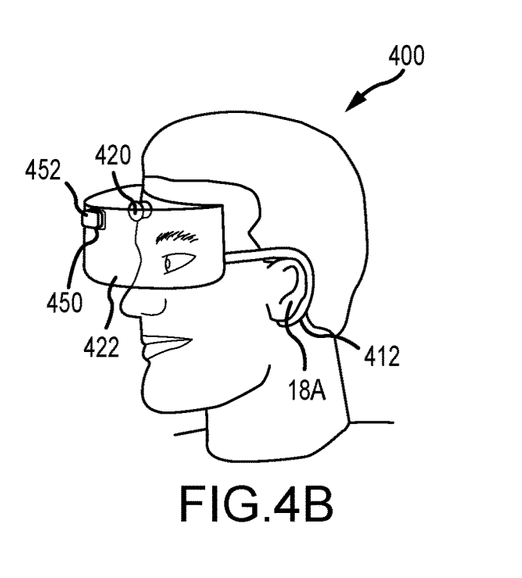
FIG. 4B is side elevation view of the HGN test device shown in FIG. 4A.
Figure 4C:
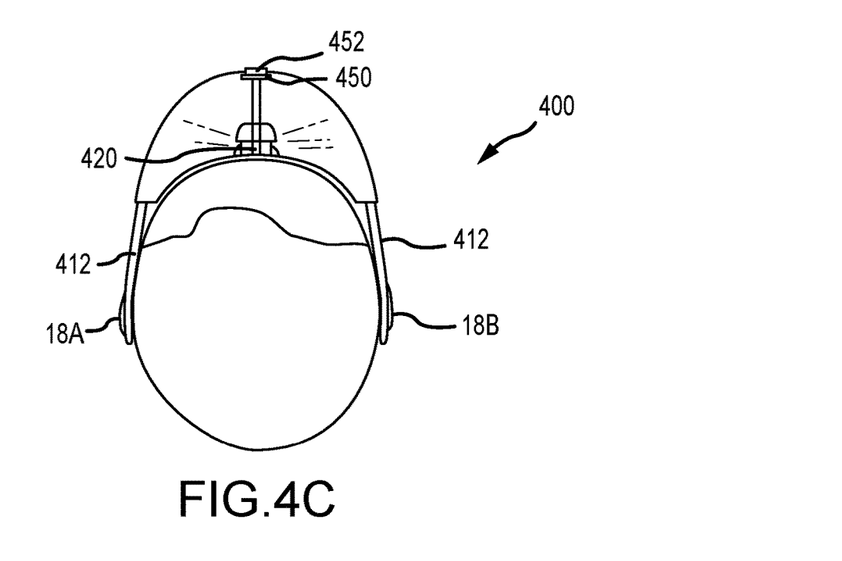
FIG. 4C is a top plan view of the HGN test device shown in FIG. 4A.

FIG. 4 illustrates a fourth embodiment 400 of an HGN test device incorporating the features described above with respect to the third embodiment 300 (such as a harness 410, a projector 420, a screen 422, a light 450, and a recording device 452), however, the HGN test device 400 has a harness 410 with side members 412 attached to and extending from the screen 422 configured to wrap around or be supported by a subject's ears 18A,18B.

Figure 5:
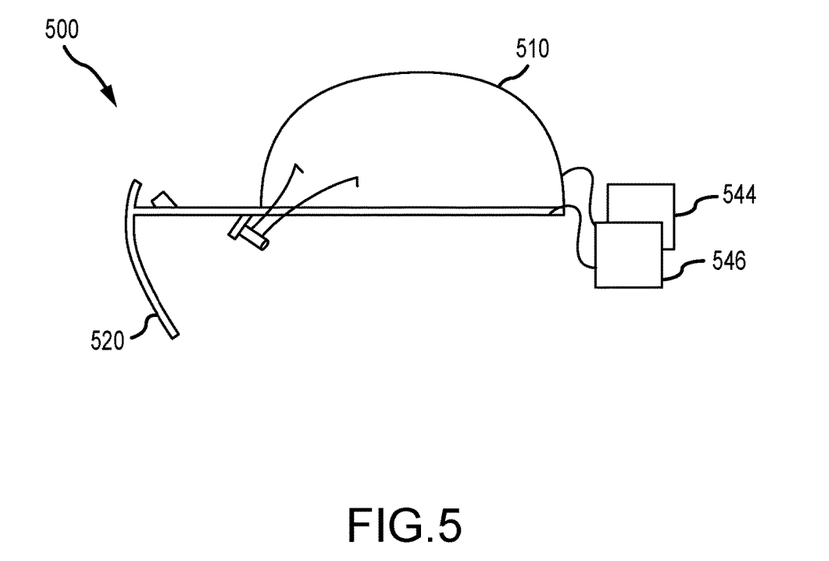
FIG. 5 is a side elevation view of a fifth embodiment of an HGN test device according to the present invention.

FIG. 5 depicts a fifth embodiment 500 of an HGN test device according to the present invention. The HGN test device 500 shown has an electronic display 520 attached to a harness 510, a computing device 544, a power supply 546. The electronic display 520 displays a point of light or object (not shown) for the eye 16A,16B of the subject 10 to follow. The displayed point of light functions just as the stimulus 140 in the first embodiment 100 and the point of light provided in the second, third, and fourth embodiments 200,300,400.

The electronic display 520 may be comprised of a plurality of LEDs, a liquid crystal display (LCD), or any type of electronic display capable of being mounted to the harness 510 and functioning in a manner as described herein. Furthermore, the elements common to those in the first embodiment 100 may be attached and configured in the same way as applied to fifth embodiment 500.

Figure 6A:
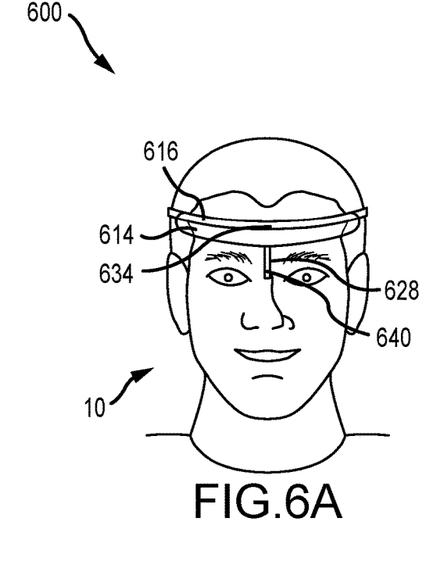
FIG. 6A is a front elevation view of a sixth embodiment of an HGN test device according to the present invention.
Figure 6B:
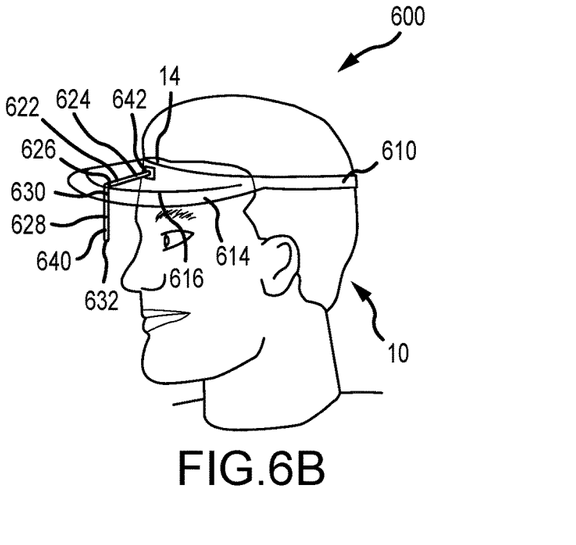
FIG. 6B is side elevation view of the HGN test device shown in FIG. 6A.
Figure 6C:
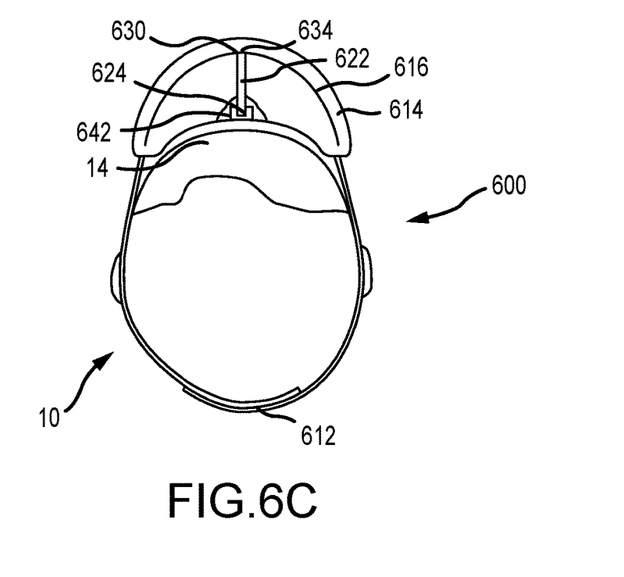
FIG. 6C is a top plan view of the HGN test device shown in FIG. 6A.

FIG. 6 provides a sixth embodiment 600 of the HGN test device. The HGN test device 600 has a harness 610 with a visor 614 and an arm 620. The harness 610 is designed to rest on the subject's head 12 and to be adjustable with adjustment straps 612.

The arm 620 preferably has a first member 622 with a first member proximal end 624 and a first member distal end 626 and a second member 628 with a second member proximal end 630 and a second member distal end 632. The first member 622 preferably extends substantially perpendicular from the face 14 of a subject 10 with the first member proximal end 624 operatively connected with a motor 642 positioned approximately at the top of the middle of the subject's face 14. The second member proximal end 630 is preferably coupled to the first member distal end 626 at a junction 634, with the second member 628 extending substantially perpendicular from the first member 622 and downward from the visor 614. The second member distal end 632 preferably has a stimulus 640 attached to the second member 628 at or near the second member distal end 632.

The visor 614 has a track 616 extending about the near periphery of the visor 614 in a mostly semi-circular pattern. The arm 620 is received within the track 616 preferably at or near the junction 634 of the first member distal end 626 and the second member proximal end 630. The first member 622 is preferably configured to extend and contract from the motor 642 as the arm 620 traverses the track 616.

The stimulus 640 may be a small pigmented ball and/or a light source such as a light emitting diode (LED) mounted to the second member distal end. Additionally, or alternatively, the stimulus 640 may comprise a plurality of LED lights stacked in a row along the second member 628.

Although not shown in FIG. 6, the HGN test device 600 may also include a recording device, a light, and a computing device as provided in the description of the first embodiment 100.

The foregoing is considered as illustrative only of the principles of the invention. Furthermore, because numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. An apparatus for administering a horizontal gaze nystagmus (HGN) test, the apparatus comprising:
    a harness configured to fit a human head;
    an armature assembly extending from a first mounted end coupled to the harness to a second free end, wherein the second free end includes a terminus;
    a motor operatively coupled to the armature assembly for translating at least a portion of the armature assembly along a stimulus path;
    a controller operatively connected to the motor and programmed to cause the portion of the armature assembly to follow the stimulus path; and
    a power supply operatively coupled to the motor and controller.

2. The apparatus of claim 1, wherein the armature assembly is a jointed armature.

3. The apparatus of claim 1, wherein the motor is coupled to the armature at a point closer to the first mounted end than the second free end.

4. The apparatus of claim 1, wherein the power supply is supported by the harness.

5. The apparatus of claim 1, further including a diffused light source supported by the harness.

6. The apparatus of claim 1, wherein the distinct terminus includes a visual stimulus.

7. The apparatus of claim 6, wherein the visual stimulus is a stimulus light source.

8. The apparatus of claim 7, wherein the stimulus light source is selected from the group consisting of LED, incandescent, fluorescent light and combinations thereof.

9. The apparatus of claim 1, wherein the harness is selected from the group consisting of a baseball style cap, a hat, a banded harness, and a welder's shield.

10. The apparatus of claim 1, wherein the motor is a servo motor.

11. The apparatus of claim 1, further comprising an image recording device supported by the harness and capable of recording at least one of video and still images in a focal field that is about 5 to about 7 inches wide by about 1 to about 3 inches tall, at a distance of about 10 to about 18 inches from the terminus towards the first mounted end.

12. The apparatus of claim 11, further including an attachment device operatively configured to receive the recording device and support the recording device at least substantially stationarily with respect to the harness, whereby the recording device is selectively detachable from its coupling to the harness.

13. The apparatus of claim 11, further comprising an audio recording device supported by the harness.

* * * * *